United States Patent [19]

Gonser

[11] Patent Number: 5,062,797
[45] Date of Patent: Nov. 5, 1991

[54] ALLOY BEARING FOR DENTAL SCALER

[75] Inventor: Donald I. Gonser, Lancaster, Pa.

[73] Assignee: Den-Tal-Ez, Inc., Audubon, Pa.

[21] Appl. No.: 578,651

[22] Filed: Sep. 5, 1990

[51] Int. Cl.$^5$ ............................................... A61C 3/08
[52] U.S. Cl. .................................................. 433/118
[58] Field of Search ...................... 433/118, 120, 132;
75/955; 428/680; 420/441, 449; 148/426;
204/192.16

[56] References Cited

U.S. PATENT DOCUMENTS

| | | | |
|---|---|---|---|
| 3,811,190 | 5/1974 | Sertich | 433/118 |
| 4,330,282 | 5/1982 | Nash | 433/118 |
| 4,484,988 | 11/1984 | Robinson | 204/38.1 |

Primary Examiner—Cary E. O'Connor
Attorney, Agent, or Firm—Howson and Howson

[57] ABSTRACT

An improved rotor shaft for a vibratory dental scaling instrument. The shaft includes a metal substrate having a surface layer of nickel-boron alloy. The alloy surface layer provides a durable bearing surface for a rotor rotatably mounted on the shaft. The thus fabricated scaling instrument is capable of being heat sterilized without adverse effects on its rotary components.

14 Claims, 2 Drawing Sheets

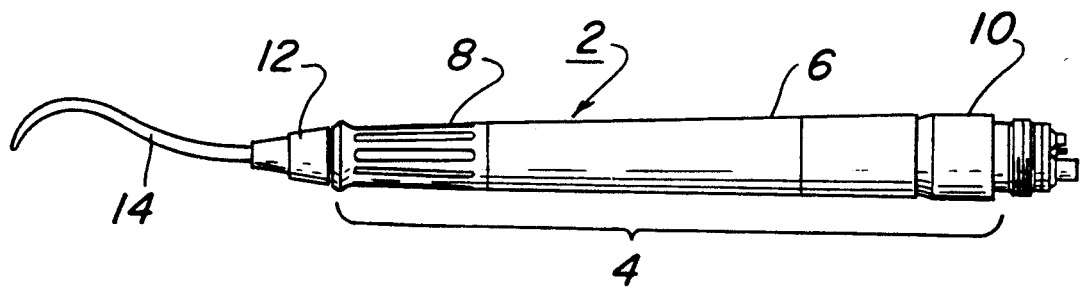
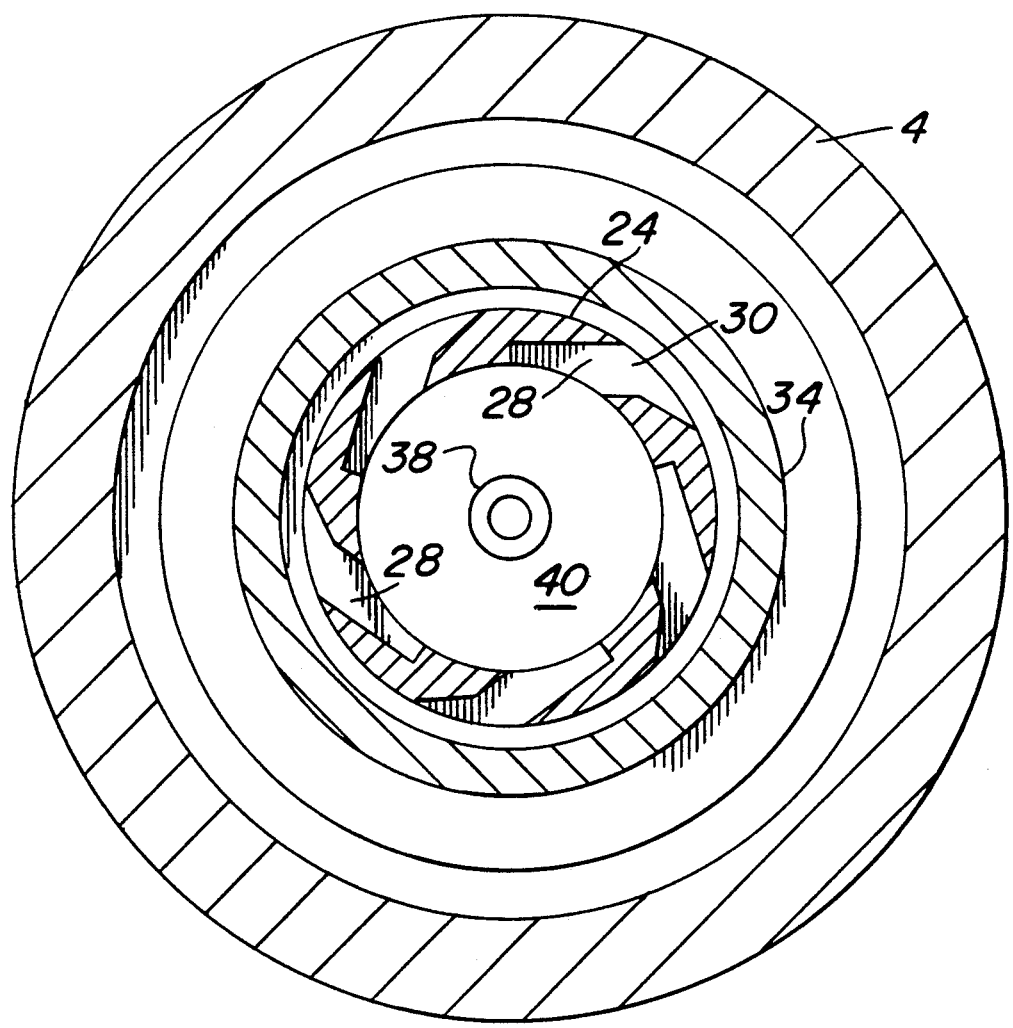

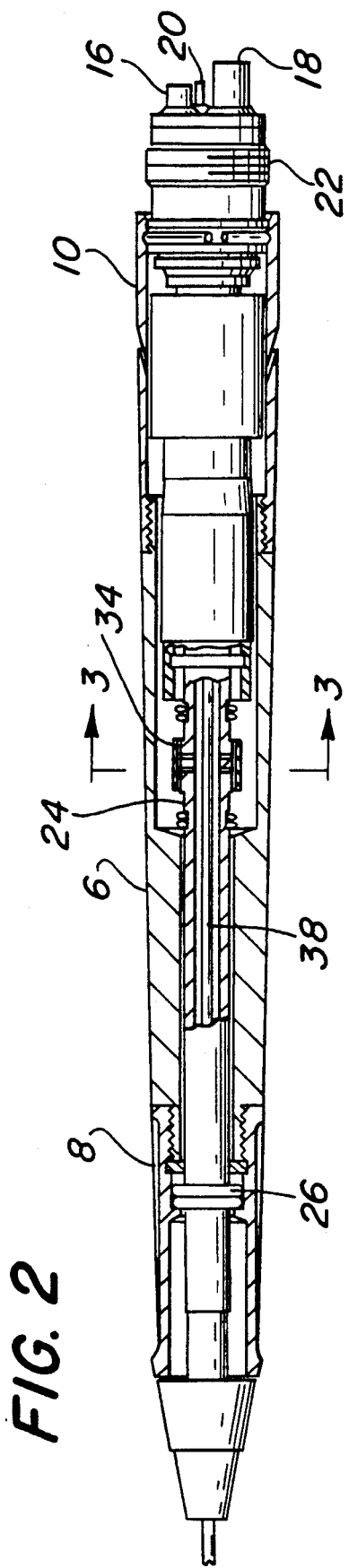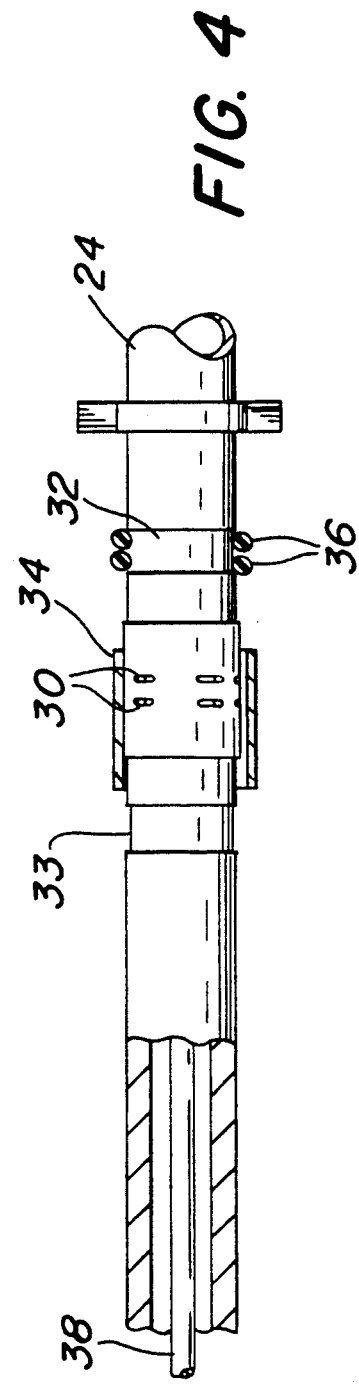

ALLOY BEARING FOR DENTAL SCALER

FIELD OF THE INVENTION

This invention relates to a hand-held vibratory dental scaler and more particularly to a hand-held vibratory dental scaler in which vibrations are generated by rotating an air driven sleeve-shaped rotor around a shaft located within the scaler.

BACKGROUND OF THE INVENTION

Dental scalers remove plaque from teeth by vibrations, which cause tartar to be dislodged from the teeth and the spaces between the teeth. Various types of powered dental scalers are known, the most common of which are the electrical ultrasonic transducer and the air driven sonic vibrating models. Ultrasonic scalers require complex electronic components for controlling the frequency of vibrations and are therefore quite expensive. Air driven sonic scalers are often subject to high frequency shaft vibration, which makes them subject to wear in the shaft-rotor area, thereby necessitating frequent servicing and replacement of parts.

Some models of currently available hand-held dental scalers, such as the Titan ® SW model sonic scaler, manufactured by Star Dental Products, Lancaster, Penn., remove plaque from teeth by vibrations generated by the rotation of an air-driven rotor around a shaft. In these models the rotor oscillates against the surface of the shaft, thereby creating vibrations which initiate the self resonant frequency of the shaft that in turn excites the tip of the scaler to vibrate at the same frequency. These scalers are preferred over other scalers because of their ease of use, efficiency and enhanced durability.

U. S. Pat. No. Re. 29,687, issued to Sertich, the disclosure of which is incorporated herein by reference, describes a scaler in which vibrations are generated by the rotation of a sleeve-shaped rotor around a hollow tubular shaft. The shaft has two or more rows of passages which extend radially outward from the hollow interior of the shaft to its external cylindrical surface. The rotor, which has an inside diameter slightly greater than the outside diameter of the shaft, is maintained in position over the external compressed air ports of the passages by means of air flow equilibrium. Guide rings are provided as stops for control at start-up and until the rotor stabilizes. The guide rings are mounted on the tubular shaft, one on each side of the rows of ports, and they are spaced sufficiently to permit the rotor to move back and forth slightly in opposite axial directions during rotor start-up or run-down conditions. The rotor of the Sertich scaler is rotated by directing air through the central opening of the shaft and out through the radial passages. The air is discharged from the ports in a direction somewhat tangential to the outer surface of the shaft and after it leaves the ports it impinges on the inside surface of the rotor, thereby causing the rotor to rotate at high speeds, setting the shaft into resonant vibration in a range of 5000 to 6000 Hertz. The high rate of rotation of the rotor, together with its axial and radial oscillation during rotation, causes the shaft to vibrate at about 6,000 Hertz. The vibration set up in the shaft is transmitted to the tip of the scaler.

The shafts of air-driven dental scalers having shaft-mounted sleeve rotors are desirably made of a special brass alloy because of its superior resonance properties and ease of machinability. Unfortunately, brass is very soft and cannot withstand the significant frictional forces and impacts imparted to the shaft during operation of the scaler. To eliminate this problem, it is the practice, when constructing the rotor shafts out of brass, to plate a very thin layer of a more durable metal onto the outer surface of the shaft in the rotor area. The more durable metal acts as a bearing surface for the rotor. A preferred plating metal is nickel, which, in addition to its durability, provides a smooth, corrosion resistant surface.

The current procedure for finishing dental scaler rotor shafts is to plate an alloy containing about 90% nickel and 10% phosphorus onto the surface of the shaft. It is usually necessary to further enhance the bearing properties of nickel-phosphorus alloy plated rotor shafts. One method of accomplishing this is to pit the sidewall of the plated shaft and impregnate the pitted surface with polytetrafluoroethylene, e.g. Teflon ®. The Teflon ® provides a smooth bearing surface on the shaft, thereby reducing the tendency of the shaft to undergo excessive wear.

A number of disadvantages attend the use of nickel-phosphorus alloy as a plating material for dental scaler rotors. One disadvantage is that the plated part must be heat-treated at a temperature of about 400° C. for an hour or more to harden the alloy, thus further increasing the complexity and cost of the shaft manufacturing process. A second and more serious disadvantage is that the nickel-phosphorus alloy tends to soften upon being repeatedly subjected to elevated temperatures, which, of necessity, occurs after each use because the scaler must be sterilized after use at a temperature of up to about 135° C. for an autoclave or chemiclave sterilizer. In a dry heat sterilizer, the scaler is subjected to temperatures up to 175° C. After repeated sterilizations, the nickel-phosphorus layer softens and the shaft plating wears rapidly, thereby substantially shortening its useful life. A third disadvantage is the lack of uniformity of the finished shafts. It is difficult to control accurately the degree of pitting, and the amount of Teflon ® impregnated into the surface of the shaft can vary widely from shaft to shaft. The lack of uniformity results in an inordinately high percentage of shaft rejects.

Because of the above-noted disadvantages there is a continuing effort to develop dental scaler rotor shafts which can be more simply manufactured and which have superior durability and bearing properties and which is not affected adversely by heat sterilization temperatures.

OBJECTS OF THE INVENTION

It is an object of the invention to provide a dental scaler shaft which has improved durability.

It is another object of the invention to provide a dental scaler shaft having a surface with physical properties that are unaffected by customary heat sterilization temperatures.

It is another object of the invention to provide a low cost dental scaler shaft which has a very smooth surface and which is highly resistant to wear.

It is anther object of the invention to provide a simplified method of manufacturing high quality, low cost dental scaler rotor shafts.

These and other objects and advantages of the invention will be apparent from the following summary and detailed description of the invention, when read in conjunction with the attached drawings.

SUMMARY OF THE INVENTION

Nickel plated dental scaler rotor shafts have now been developed which embody all of the above objects and which are free of the defects of the earlier shaft manufacturing processes and products.

According to the invention, low friction and superior wear resistance properties are imparted to rotor shafts for hand-held dental scalers by plating a thin uniform layer of nickel-boron alloy onto the rotor bearing surface of the shafts. The nickel boron alloy generally contains more than about 98.5% nickel and less than about 1.5% boron the percentages being by weight. In a preferred embodiment, the nickel-boron plating alloy comprises about 98.5 to about 99.5 weight percent nickel and about 1.5 to about 0.5 weight percent boron. The nickel-boron alloy may be deposited on the surface by any plating procedure; however, it is preferred to use electroless plating because this technique provides a layer of more uniform thickness. The thickness of the nickel-boron layer is generally about 0.2 to about 0.5 mil and preferably about 0.3 to about 0.4 mil. The plated layer has a hardness of about 49 Rockwell C, and a surface smoothness of about 32 microinches.

BRIEF DESCRIPTION OF THE DRAWINGS

One embodiment of the invention is illustrated in the accompanying drawings wherein: FIG. 1 is a longitudinal view of a hand-held dental scaling instrument; FIG. 2 is an enlarged cross sectional view of a portion of the scaling instrument of FIG. 1; FIG. 3 is a cross sectional view, greatly enlarged, of the scaling instrument of FIG. 1, taken along the line 3—3 of FIG. 2; and FIG. 4 is a fragmentary view of the rotor shaft of the scaling instrument of FIG. 1, which shaft incorporates the main feature of this invention.

DETAILED DESCRIPTION OF THE INVENTION

Referring to the drawings, the hand-held dental scaler 2 includes a barrel 4 which has a handle section 6 for gripping the scaler, a tip section 8 and a coupling section 10. Tip section 8 is adapted to receive scaling tools, such as tool 12. The scaling tools can have a variety of shapes, of which the sickle-shaped tool tip 14 shown in FIG. 1 is one example.

Coupling section 10 provides mean for coupling the scaling instrument to the fluid streams necessary for the operation of the instrument. In the embodiment illustrated in the drawings, which is driven by compressed air and cooled by water, coupling section 10 is provided with a drive air conduit 16, an air exhaust conduit 18 and a cooling water conduit 20, best seen in FIG. 2. Coupling section 10 also has means, such as threaded section 22, for attaching the scaling instrument to an air and water supply manifold (not shown).

Referring now to FIGS. 2-4, a vibratable hollow cylindrical shaft 24 is disposed longitudinally within barrel 4. Shaft 24 is positioned concentrically within barrel 4, and it is maintained in axial alignment by tip end support means 26 and coupling end support means (not shown). Tip end support means 26 also serves to form a fluid-tight seal between the outside wall of shaft 24 and the inside wall of tip end 8. As illustrated in FIGS. 3 and 4, shaft 24 has a series of bored passages 28 which provide fluid communication through the sidewall of shaft 24. Passages 28 exit the cylindrical surface of shaft 24 through ports 30, which are disposed circumferentially around the shaft, preferably in two or more parallel rows of ports. Passages 28 are bored through the wall of shaft 24 at an angle of less than 90 degrees, so that air passing through passages 28 from the interior of shaft 24 to its exterior will provide a thrust in a direction somewhat tangent to the outside wall of shaft 24.

The sidewall of shaft 24 has a pair of circumferential grooves 32, 33 located on each side of ports 30. A cylindrical sleeve rotor 34 is disposed concentrically around shaft 24 and positioned over ports 28. The inside diameter of rotor 34 is great enough to permit the rotor to freely rotate around shaft 24 and to oscillate in a radial direction. One or more "O" rings 36, made of an elastomeric material, all positioned in each groove 32 and 33. Rings 36 are large enough to hold rotor 34 in position over ports 30. Grooves 32 and 33 are longitudinally spaced from each other a sufficient distance to allow limited longitudinal movement of rotor 34.

A hollow elongate tube 38 is disposed within shaft 24 and extends from the tip section end 8 to the coupling section end 10. On its coupling section end, tube 38 is in fluid communication with water conduit 20, and, on its tip end, it communicates with an opening in tool 12. Tube 38 serves to carry water to tool 12 for cooling purposes. The water exits tool 12 through an opening (not shown) and provides a stream of water for flushing away tartar which is dislodged during scaling operations. Tube 38 is maintained in axial alignment by support means located at each end of the tube (not shown). The tube tip end support means also serves as a fluid seal between the outer sidewall of tube 38 and the inner sidewall of shaft 24.

The scaling instrument is operated by connecting it to an air/water hose coupling and adjusting the air and water flow rates to the desired values (about 1.5 standard cubic feet of air per minute (scfm) at a pressure of about 40 pounds per square inch gauge (psig) and about 25 cc of water per minute at a pressure of about 15 (psig). Under these conditions the rotor will rotate at a rate of about 5000 to 6000 revolutions per second (rps). During operation, water enters conduit 20, passes through water tube 38 and exits the instrument through the opening in scaling tool 12. At the same time compressed air enters drive air conduit 16 and passes into the annular space 40 between the outside wall of water tube 38 and the inside wall of shaft 24. The air passes radially outwardly through passages 28 and ports 30. The air leaving ports 30 impinges against the inside wall of rotor 34, thereby causing it to rotate. The spent air passes out through the end openings of rotor 34 and into the annular space between the outside wall of shaft 24 and the inside wall of barrel 4. The air then passes out of the scaling instrument through exhaust air conduit 18.

As the dental scaler operates, rotor 34, in addition to rotating, oscillates in both the axial and radial direction. As it rotates and oscillates, it repeatedly impacts against shaft 24, thereby producing the vibrations which cause tarter to be dislodged from the teeth of the patient being treated. It can be appreciated that the outside surface of shaft 24, particularly in the zone between grooves 32 and 33 must be both durable and very smooth. As noted above, the rotor shafts currently in use are deficient in these properties.

The improved rotor shafts of this invention are comprised of a substrate and a nickel-boron alloy coating over the substrate. The substrate can be made from any metallic or non-metallic substance which possesses the strength, toughness and machinability required of dental scaler rotor shafts, and which also possesses the properties necessary to transmit, without substantial diminution, the vibrations imparted to the shaft by the rotor during operation of the scaler. As noted above, the preferred metal is brass because of its superior resonance properties. However, other materials such as stainless steel, titanium, beryllium and nickel alloys, etc., may be employed if less than all the advantages of using brass are acceptable.

The nickel-boron coating need only be applied over the rotor bearing surface, i.e. the area of shaft 24 which underlies rotor 34, to realize the benefits of the invention. However, it is generally more practical and economical to coat the entire external surface of shaft 24 with the nickel-boron alloy. The thickness of the nickel-boron alloy coating on the surface is not critical. Since nickel-boron is very hard and wear resistant any coating which is thick enough to provide a substantially continuous coating will be satisfactory. The upper coating thickness limit is dictated by economics and diametric specifications. In general, the thickness of the nickel-boron coating is desirably in the range of about 0.2 to about 0.5 mil and preferably in the range of about 0.3 to about 0.4 mil. Desirably, the coating has a hardness in a range of 48 to 50 Rockwell C, and a surface finish of 32 microinches.

The nickel-boron alloy is comprised of about 98.5 to about 99.5 weight percent nickel and about 0.5 to about 1.5 weight percent boron. In a preferred embodiment the boron content of the alloy is not greater than about 1.0 weight percent. It has been found that nickel-boron alloys containing up to about 1 weight percent boron have high temperature resistance, high hardness, and excellent wear resistance properties and these alloys also retain the smoothness and corrosion resistance properties of nickel. Because of these advantages, nickel-boron alloy rotor shafts can be heat sterilized a great many times at high temperatures. Furthermore, the nickel-boron shafts are less costly to manufacture because of their lower sensitivity to manufacturing specification variations.

The nickel-boron alloy can be applied to the shafts by any of the commercially feasible metal-coating procedures, such as electroplating or electroless plating. The preferred method of applying the alloy coating to the shafts is electroless plating because of the uniformity and continuity of electroless coatings. Electroless plating may be accomplished by the procedure described below, which, although a referred procedure, is merely exemplary and is not intended to be limiting.

According to the preferred procedure, the shafts are first cleaned, as by soaking them in a strong alkaline cleaning solution, to remove dirt and grease. The clean shafts are then rinsed in water and dipped in an acid bath to activate the surface being plated. After the acid treatment the shafts are rinsed in water and electrolessly plated with a suitable nickel-boron alloy in accordance with any of the well known techniques. A particularly useful nickel-boron alloy electroless plating technique is the system marketed by Witco Corporation under the designation Niklad TM 752 electroless nickel-boron system.

The invention is further illustrated by the following specific example.

Nine No. 464 naval brass dental rotor shafts which were electrolessly plated with nickel-phosphorus alloy and the plated surface pitted and filled with polytetrafluoroethylene were tested and found to be unsuitable for use in dental scalers because rotors would not rotate properly when mounted on the shafts. Upon examination under a microscope it was observed that the nickel-phosphorus coating was of poor quality and the size of the pits was large and irregular. The nickel-phosphorus alloy layer was chemically stripped from the shafts and they were electrolessly plated with nickel-boron alloy. Upon retesting, all nine of the newly plated shafts passed performance specification tests. One of the re-plated shafts was subjected to a life test and found to operate satisfactorily for a period of 2500 cycle hours. In contrast, the typical life for nickel-phosphorus plated shafts is between 1000 and 2000 hours. A cycle hour is composed of one minute sub cycles, each involving a start-up, a run for 45 seconds, and a run down and stop for 15 seconds.

The above example illustrates some of the benefits derived from practice of the invention. The dental rotor shafts of the invention are simpler and less costly to manufacture and usually have a 25% or more longer useful life than the longest the average life of nickel-phosphorus plated shafts.

Although the invention is illustrated with particular reference to a specific example, variations are considered to be within the scope of the invention. For example, a thicker nickel-boron layer may be applied on the section of the shaft which provides a bearing surface for the rotor than on the rest of the shaft. The scope of the invention is limited only by the breadth of the appended claims.

What is claimed is:

1. In a dental scaler having a rotor rotatable about a shaft and operably engageable therewith to produce vibrations, the improvement comprising a nickel-boron alloy layer comprising from about 98.5 to about 99.5 weight percent nickel and from about 1.5 to about 0.5 weight percent boron, based on the total weight of said nickel-boron alloy, interposed between the rotor and the shaft to provide a wear resistant, low friction bearing surface.

2. The shaft of claim 1 wherein said nickel-boron alloy layer is formed by electroless plating on said shaft.

3. The shaft of claim 2 wherein said nickel-boron alloy outer layer is about 0.2 to about 0.5 mil thick.

4. The shaft of claim 1 wherein said shaft is made of metal and said layer is on said shaft.

5. The shaft of claim 4 wherein said metal is brass.

6. A shaft for a vibratory dental scaling instrument comprising a hollow cylindrical member having a layer of nickel-boron alloy on its outer periphery, said nickel-boron alloy layer comprising from about 98.5 to about 99.5 weight percent nickel and about 1.5 to about 0.5 weight percent boron, based on the total weight of the alloy, and being adapted to provide a bearing surface for a rotor sleeve rotatably operably engaging said shaft.

7. The shaft of claim 6 wherein the thickness of said nickel-boron alloy layer is in a range of about 0.2 to about 0.5 mils.

8. A hollow metal shaft for a fluid-operated vibratory dental scaler, said shaft having at least one series of passages extending radially outward from its hollow center to its periphery in a direction enabling a fluid to be discharged through said passages to impart rotary motion to a rotor rotatable in a path surrounding said passages, said metal shaft having a nickel-boron alloy peripheral surface at least in the region of said path of rotation, such nickel-boron alloy containing at least about 98.5 weight percent nickel, and having a thickness in a range of about 0.2 to about 0.5 mils and a surface smoothness of about 32 micro inches.

9. The shaft of claim 8 comprising a layer of brass with said layer of nickel-boron alloy surrounding said brass layer.

10. The shaft of claim 8 having means on each side of said series of passages adapted to maintain a cylindrical rotor in position over said series of passages.

11. The shaft of claim 10 wherein said means comprises one or more circumferential grooves on each side of said series of passages.

12. In an air driveable vibration generator for a dental scaler comprising a vibratable shaft having a bearing surface on its outer periphery and a rotor rotatably mounted on said shaft having an inner surface adapted to impact against said bearing surface as the rotor rotates, the improvement wherein at least one of said surfaces comprises a nickel-boron alloy, containing from about 98.5 to about 99.5 weight percent nickel and from about 1.5 to about 0.5 weight percent boron, a thickness of said nickel-boron alloy in a range of about 0.3 to about 0.4 mil, a hardness in the range of about 48 to about 52 Rockwell C, and a surface smoothness of about 32 microinches.

13. The improved vibration generator of claim 12 wherein said shaft comprises a layer of brass and said one surface includes a layer of nickel-boron alloy on said brass layer.

14. The improved vibration generator of claim 13 wherein said nickel-boron alloy is electrolessly plated on said brass layer.

* * * * *